(12) United States Patent
Ward

(10) Patent No.: US 11,457,939 B2
(45) Date of Patent: Oct. 4, 2022

(54) FORCEPS BLADE CONTROL

(71) Applicant: GYRUS ACMI, INC., Southborough, MA (US)

(72) Inventor: Zane R. Ward, Minneapolis, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 309 days.

(21) Appl. No.: 16/829,545

(22) Filed: Mar. 25, 2020

(65) Prior Publication Data

US 2020/0305907 A1 Oct. 1, 2020

Related U.S. Application Data

(60) Provisional application No. 62/994,220, filed on Mar. 24, 2020, provisional application No. 62/841,476, (Continued)

(51) Int. Cl.
*A61B 17/29* (2006.01)
*A61B 17/28* (2006.01)
(Continued)

(52) U.S. Cl.
CPC ........ *A61B 17/282* (2013.01); *A61B 17/1285* (2013.01); *A61B 17/2804* (2013.01);
(Continued)

(58) Field of Classification Search
CPC .............. A61B 17/282; A61B 17/1285; A61B 17/2804; A61B 17/2833; A61B 17/285; A61B 17/29; A61B 17/2909; A61B 17/295; A61B 18/1445; A61B 18/149; A61B 18/1447; A61B 90/03; A61B 2017/2845; A61B 2017/2901; A61B 2017/2902; A61B 2017/2903; A61B 2017/2908; A61B 2017/2916; A61B 2017/2917; A61B 2017/2919; A61B 2017/292;
(Continued)

(56) References Cited

U.S. PATENT DOCUMENTS 4,887,612 A 12/1989 Esser et al.
6,458,130 B1 10/2002 Frazier et al.
(Continued)

FOREIGN PATENT DOCUMENTS

WO WO-2009070780 A1 6/2009

OTHER PUBLICATIONS

"U.S. Appl. No. 16/830,150, Examiner Interview Summary dated Dec. 10, 2021", 3 pgs.
(Continued)

*Primary Examiner* — Erich G Herbermann
(74) *Attorney, Agent, or Firm* — Schwegman Lundberg & Woessner, P.A.

(57) ABSTRACT

A surgical tool can include a shaft, a pin, an end effector, and a translating member. The shaft can define a longitudinal axis. The pin can be located at a distal portion of the shaft. The end effector can be connected to the shaft. The translating member can be positioned laterally inward of the shaft. The translating member can include a track and the pin can extend into the track to limit translation of the translating member along the longitudinal axis with respect to the end effector.

20 Claims, 8 Drawing Sheets

Distal                                                                                    Proximal

Related U.S. Application Data filed on May 1, 2019, provisional application No. 62/826,522, filed on Mar. 29, 2019, provisional application No. 62/826,532, filed on Mar. 29, 2019.

(51) Int. Cl.

| | | |
|---|---|---|
| *A61B 18/14* | (2006.01) | |
| *A61B 17/128* | (2006.01) | |
| *A61B 90/00* | (2016.01) | |
| *A61B 17/285* | (2006.01) | |
| *B23K 26/21* | (2014.01) | |
| *A61B 17/32* | (2006.01) | |
| *A61B 17/295* | (2006.01) | |
| *A61B 18/00* | (2006.01) | |

(52) U.S. Cl.
CPC ........ *A61B 17/285* (2013.01); *A61B 17/2833* (2013.01); *A61B 17/29* (2013.01); *A61B 17/2909* (2013.01); *A61B 18/149* (2013.01); *A61B 18/1445* (2013.01); *A61B 90/03* (2016.02); *B23K 26/21* (2015.10); *A61B 17/295* (2013.01); *A61B 18/1447* (2013.01); *A61B 2017/2845* (2013.01); *A61B 2017/2901* (2013.01); *A61B 2017/2902* (2013.01); *A61B 2017/292* (2013.01); *A61B 2017/2903* (2013.01); *A61B 2017/2908* (2013.01); *A61B 2017/2916* (2013.01); *A61B 2017/2917* (2013.01); *A61B 2017/2919* (2013.01); *A61B 2017/2925* (2013.01); *A61B 2017/2926* (2013.01); *A61B 2017/2933* (2013.01); *A61B 2017/2936* (2013.01); *A61B 2017/2945* (2013.01); *A61B 2017/2946* (2013.01); *A61B 2017/2947* (2013.01); *A61B 2017/2948* (2013.01); *A61B 2017/320052* (2013.01); *A61B 2017/320095* (2017.08); *A61B 2018/0063* (2013.01); *A61B 2018/0091* (2013.01); *A61B 2018/00148* (2013.01); *A61B 2018/00196* (2013.01); *A61B 2018/00202* (2013.01); *A61B 2018/00309* (2013.01); *A61B 2018/00345* (2013.01); *A61B 2018/00601* (2013.01); *A61B 2018/00636* (2013.01); *A61B 2018/00916* (2013.01); *A61B 2018/00946* (2013.01); *A61B 2018/00952* (2013.01); *A61B 2018/1412* (2013.01); *A61B 2018/1455* (2013.01); *A61B 2018/1457* (2013.01); *A61B 2090/034* (2016.02)

(58) Field of Classification Search
CPC .... A61B 2017/2925; A61B 2017/2926; A61B 2017/2933; A61B 2017/2935; A61B 2017/2945; A61B 2017/2946; A61B 2017/2947; A61B 2017/2948; A61B 2017/320052; A61B 2018/00601; A61B 2018/1412; A61B 2018/1457
See application file for complete search history.

(56) References Cited

U.S. PATENT DOCUMENTS

| | | | |
|---|---|---|---|
| 7,131,971 B2 | 11/2006 | Dycus et al. | |
| 8,382,754 B2 | 2/2013 | Odom et al. | |
| 8,540,711 B2 | 9/2013 | Dycus et al. | |
| 8,663,270 B2 | 3/2014 | Donnigan et al. | |
| 8,715,277 B2 | 5/2014 | Weizman | |
| 8,968,311 B2 | 3/2015 | Allen, IV et al. | |
| 8,968,313 B2 | 3/2015 | Larson | |
| 9,636,169 B2 | 5/2017 | Allen, IV et al. | |
| 9,681,883 B2 | 6/2017 | Windgassen et al. | |
| 9,820,765 B2 * | 11/2017 | Allen, IV | A61B 17/282 |
| 2003/0018331 A1 | 1/2003 | Dycus et al. | |
| 2005/0119655 A1 | 6/2005 | Moses et al. | |
| 2010/0010512 A1 | 1/2010 | Taylor et al. | |
| 2010/0057085 A1 | 3/2010 | Holcomb et al. | |
| 2010/0179545 A1* | 7/2010 | Twomey | A61B 18/1445 606/51 |
| 2010/0274244 A1 | 10/2010 | Heard | |
| 2011/0184405 A1 | 7/2011 | Mueller | |
| 2012/0059375 A1* | 3/2012 | Couture | A61B 18/1442 606/51 |
| 2014/0025071 A1 | 1/2014 | Sims et al. | |
| 2014/0276803 A1* | 9/2014 | Hart | A61B 18/1445 606/45 |
| 2016/0015419 A1 | 1/2016 | Hibner et al. | |
| 2019/0175256 A1 | 6/2019 | Butler | |
| 2019/0298399 A1 | 10/2019 | Boone et al. | |
| 2020/0305911 A1 | 10/2020 | Pham et al. | |

OTHER PUBLICATIONS

"U.S. Appl. No. 16/830,150, Final Office Action dated Mar. 30, 2022", 19 pgs.
"U.S. Appl. No. 16/830,150, Non Final Office Action dated Oct. 29, 2021", 15 pgs.
"U.S. Appl. No. 16/830,150, Response filed Dec. 10, 2021 to Non Final Office Action dated Oct. 29, 2021", 13 pgs.

* cited by examiner

FORCEPS BLADE CONTROL

CLAIM OF PRIORITY

This patent application claims the benefit of priority, under 35 U.S.C. Section 119(e), to U.S. Ser. No. 62/826,532, filed on Mar. 29, 2019, entitled "BLADE ASSEMBLY FOR FORCEPS", and to U.S. Ser. No. 62/826,522 filed on Mar. 29, 2019, entitled "SLIDER ASSEMBLY FOR FORCEPS", the disclosure of which is incorporated by reference in its entirety, and to U.S. Ser. No. 62/841,476, filed on May 1, 2019, entitled "FORCEPS WITH CAMMING JAWS", and to U.S. Ser. No. 62/994,220, filed on Mar. 24, 2020, entitled "FORCEPS DEVICES AND METHODS", each of which is hereby incorporated by reference herein in its entirety.

BACKGROUND

Medical devices for diagnosis and treatment, such as forceps, are often used for medical procedures such as laparoscopic and open surgeries. Forceps can be used to manipulate, engage, grasp, or otherwise affect an anatomical feature, such as a vessel or other tissue of a patient during the procedure. Forceps often include an end effector that is manipulatable from a handle of the forceps. For example, jaws located at a distal end of a forceps can be actuated via elements of the handle between open and closed positions to thereby engage the vessel or other tissue. Forceps can include an extendable and retractable blade that can be extended distally between a pair of jaws to lacerate the tissue. The handle can also be capable of supplying an input energy, such as electromagnetic energy or ultrasound, to the end effector for sealing of the vessel or tissue during the procedure.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Electrosurgical forceps often include a blade for cutting tissue. The blade can be positioned within a shaft of the forceps and can be operated from a handle of the forceps to extend between jaws of the forceps to cut tissue between the jaws. During use, the blade can be translated between a fully retracted (proximal) position and a fully extended (distal position). The fully extended distal position of the blade often must be limited to avoid contact between a distal (sharpened) tip or edge of the blade and components of the jaw. Such contact can damage or otherwise cause the blade to dull, which can reduce cutting effectiveness of the blade and therefore of the forceps. Blade stops exist for controlling distal extension of the blade; however, such blade stops often require one or more additional components to act as a blade stop. Such components can increase product complexity and ultimately product cost.

The present disclosure can help to address these issues by using a pin, such as a pivot pin, of the forceps to limit distal translation of the blade. In this way, a component used for coupling jaws to a shaft of the forceps (or for acting as a pivot for the jaws) can additionally be used to control distal blade travel, which can help reduce a total number of components of the forceps, helping to save cost.

The above discussion is intended to provide an overview of subject matter of the present patent application. It is not intended to provide an exclusive or exhaustive explanation of the invention. The description below is included to provide further information about the present patent application.

Figure 1:
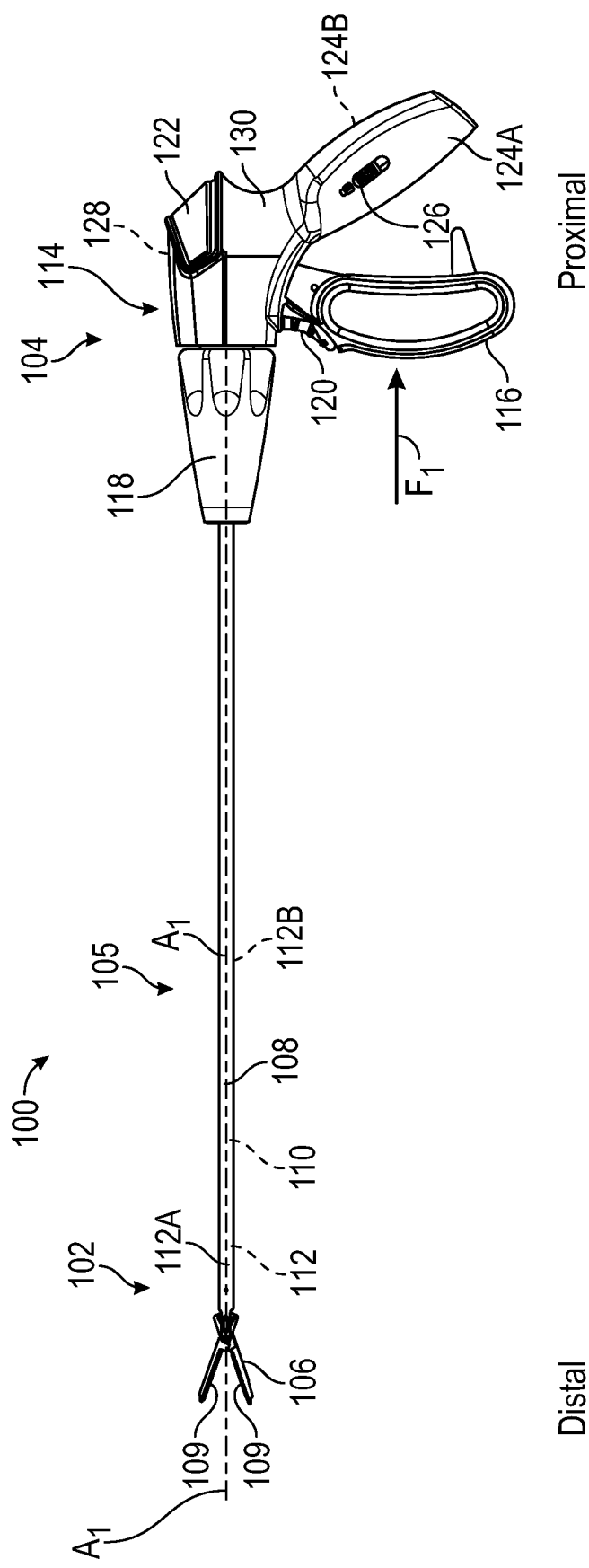
FIG. 1 illustrates a side view of a forceps showing jaws in an open position.

FIG. 1 illustrates a side view of a forceps 100 showing jaws in an open position. The forceps 100 can include an end effector 102, a handpiece 104, and an intermediate portion 105. The end effector 102 can include jaws 106 (including electrodes 109), an outer shaft 108, an inner shaft 110, and a blade assembly 112. The handpiece 104 can include a housing 114, a lever 116, a rotational actuator 118, a trigger 120, an activation button 122, a fixed handle 124a and 124b, and a handle locking mechanism 126. The housing 114 can include a first housing portion 128, and a second housing portion 130. FIG. 1 also shows orientation indicators Proximal and Distal and a longitudinal axis A1.

Generally, the handpiece 104 can be located at a proximal end of the forceps 100 and the end effector 102 can be located at the distal end of the forceps 100. The intermediate portion 105 can extend between the handpiece 104 and the end effector 102 to operably couple the handpiece 104 to the end effector 102. Various movements of the end effector 102 can be controlled by one or more actuation systems of the handpiece 104. For example, the end effector 102 can be rotated along the longitudinal axis A1 of the forceps 100. Also, the handpiece can operate the jaws 106, such as by moving the jaws 106 between open and closed position. The handpiece 104 can also be used to operate the blade assembly 112 for cutting tissue and can operate the electrode 109 for applying electromagnetic energy to tissue. The end effector 102, or a portion of the end effector 102, can be one or more of: opened, closed, rotated, extended, retracted, and electromagnetically energized.

The housing 114 can be a frame that provides structural support between components of the forceps 100. The housing 114 is shown as housing at least a portion of the actuation systems associated with the handpiece 104 for actuating the end effector 102. However, some or all of the actuation components need not be housed within the housing 114 The housing 114 can provide a rigid structure for attachment of components, but the housing 114 does not necessarily house the components completely, or can house a portion of one or more of the components.

The drive shaft 110 can extend through the housing 114 and out of a distal end of the housing 114, or distally beyond housing 114. The jaws 106 can be connected to a distal end of the drive shaft 110. The outer shaft 108 can be a hollow tube positioned around the drive shaft 110. A distal end of the outer shaft 108 can be located adjacent the jaws 106. The distal ends of the drive shaft 110 and the outer shaft 108 can be rotationally locked to the jaws 106. The rotational actuator 118 can be positioned around the distal end of the housing 114. The outer shaft 108 can extend distally beyond the rotational actuator 118. The blade shaft 112b can extend through the drive shaft 110 and the outer shaft 108. A distal end of the blade shaft 112b can be located near the jaws 106. A proximal end of the blade shaft 112b can be within housing 114.

The handpiece 104 can enable a user to extend and retract a blade 112a of the blade assembly 112, which can be attached to a distal end of a blade shaft 112b of the blade assembly 112. In some examples, the blade 112a can extend an entirety of a length between the handle 104 and the end effector 102. In some examples, the handpiece 104 can include features that inhibits the blade assembly 112 from being extended until the jaws 106 are at least partially closed, or fully closed. The blade 112a can be extended by displacing the trigger 120 proximally and the blade 112a can be retracted by allowing the trigger 120 to return distally to a default position.

A proximal portion of the trigger 120 can be connected to the blade shaft 112b within the housing 114 and a distal portion of the trigger 120 can extend outside of the housing 114 adjacent to, and in some examples nested with, the lever 116 in the default or unactuated positions. The activation button 122 can be coupled to the housing 114 and can include or be connected to electronic circuitry within the housing 114. Such circuitry can send or transmit electromagnetic energy through forceps 100 to the jaws 106. In some examples, the electronic circuitry may reside outside the housing 114 but can be operably coupled to the housing 114 and the end effector 102.

In operation of the end effector 100, a user can displace the lever 116 proximally by applying a Force F1 to the lever 116 to actuate the drive shaft 110 to drive the jaws 106 from the open position (FIG. 2C) to the closed position (FIG. 2A), which can allow the user to clamp down on and compress a tissue. The handpiece 104 can also allow a user to rotate the rotational actuator 118 to cause the end effector 102 to rotate, such as by rotating both the drive shaft 26 and the outer shaft 28 together.

In some examples, with the tissue compressed, a user can depress the activation button 122 to cause an electromagnetic energy, or in some examples, ultrasound, to be delivered to the end effector 102, such as to the electrode 109 and to the tissue. Application of such energy can be used to seal or otherwise affect the tissue being clamped. In some examples, the electromagnetic energy can cause tissue to be coagulated, sealed, ablated, desiccated or can cause controlled necrosis. When desired, the trigger 120 can be moved to translate the blade assembly 112 distally such that the blade 112a can extend between the jaws 106 in order to cut the tissue within the jaws 106. Such a process can be repeated, as desired.

In some examples, the forceps 100, or other medical device, may not include all the features described or may include additional features and functions, and the operations may be performed in any order. The handpiece 104 can be used with a variety of other end effectors to perform other methods.

Figure 2A:
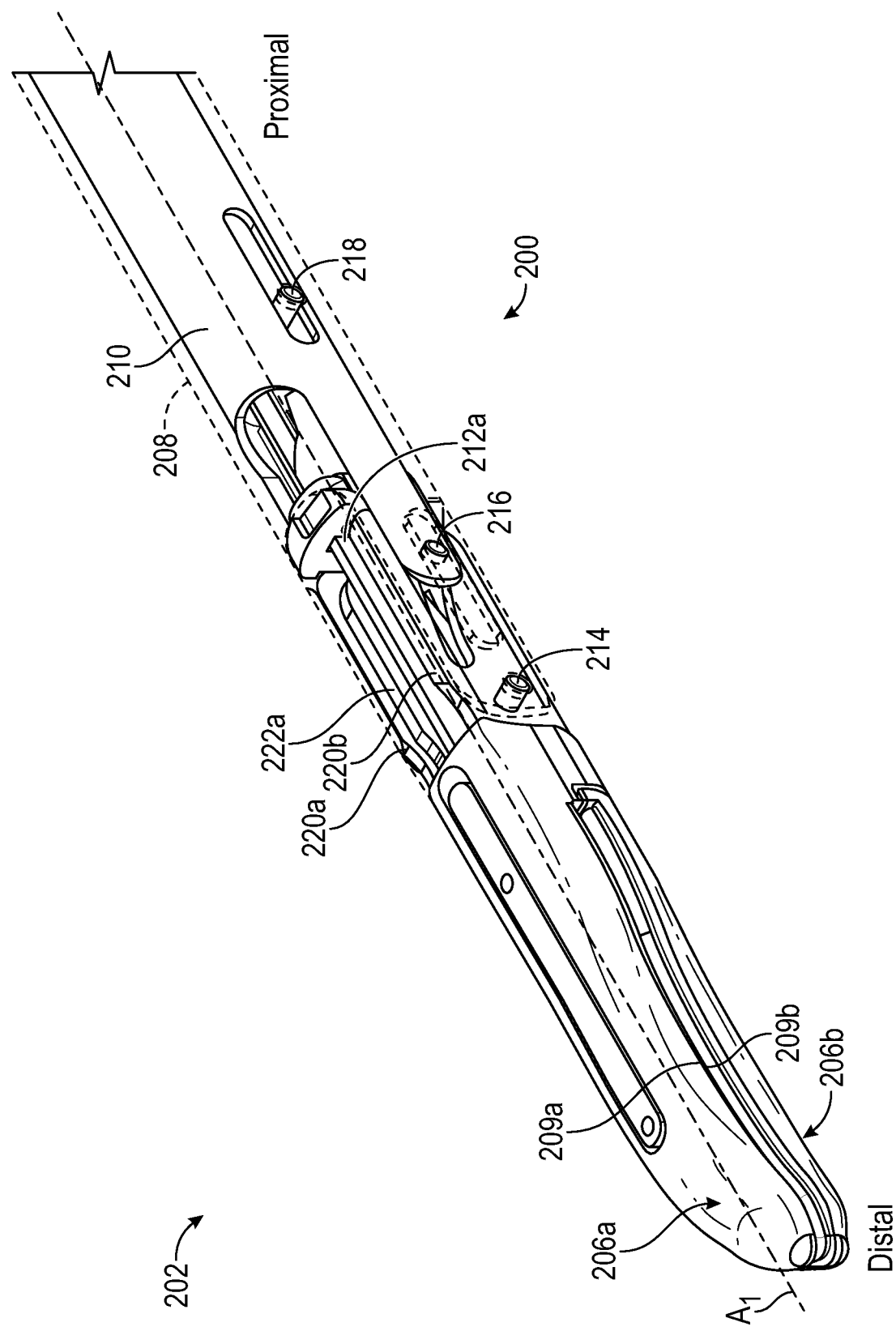
FIG. 2A illustrates an isometric view of a portion of forceps in a closed position.
Figure 2B:
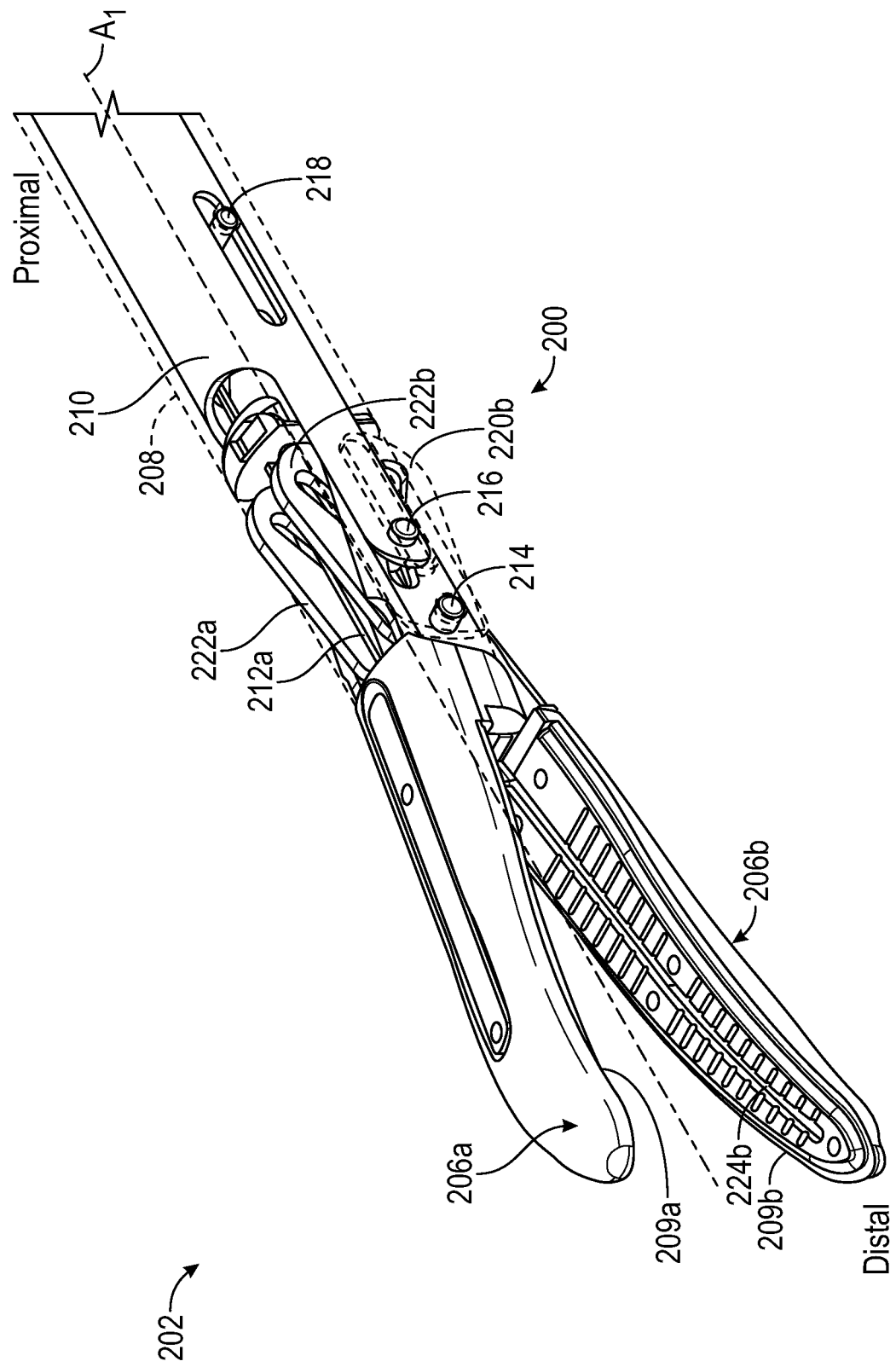
FIG. 2B illustrates an isometric view of a portion of forceps in a partially open position.
Figure 2C:
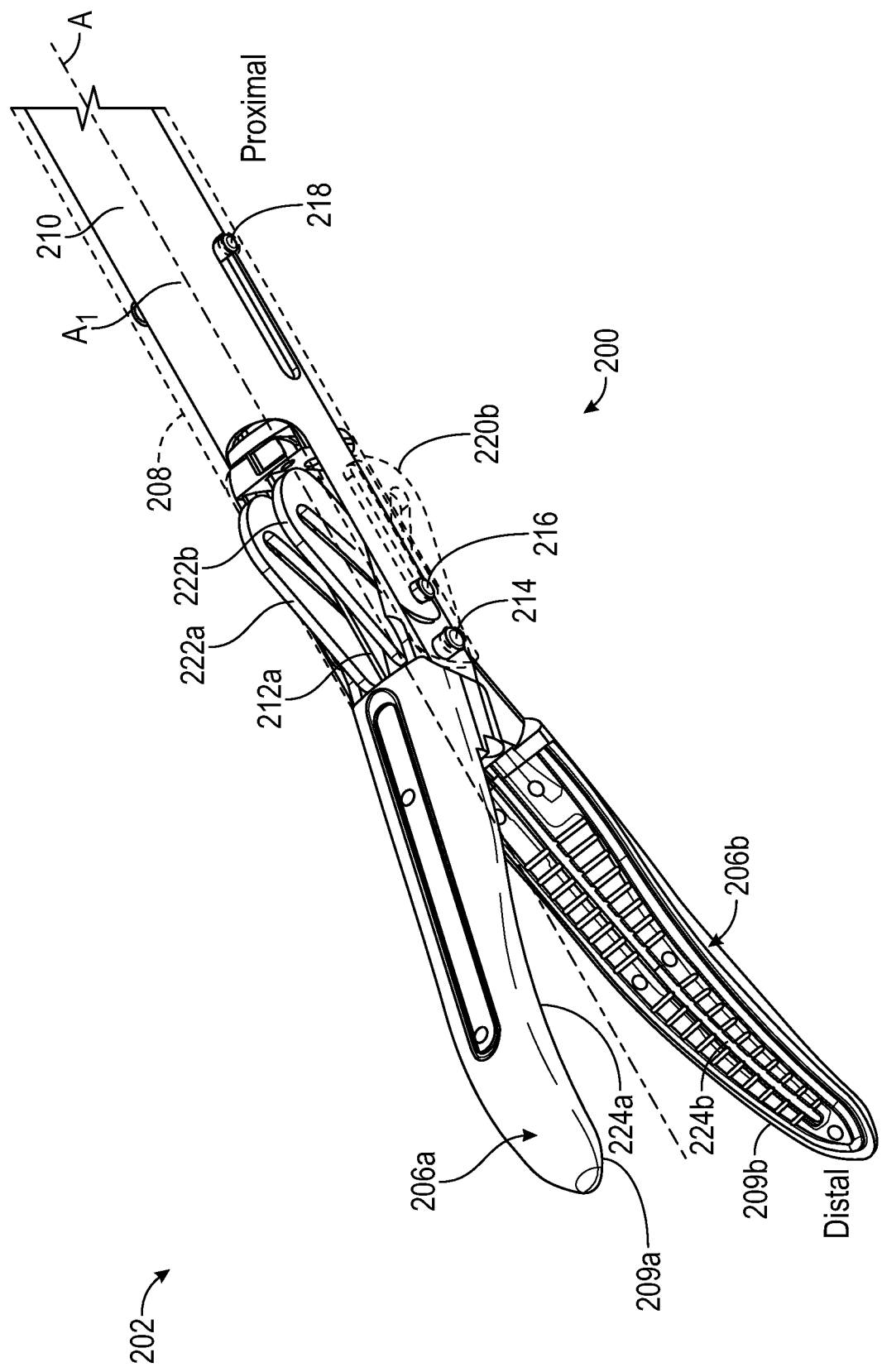
FIG. 2C illustrates an isometric view of a portion of forceps in an open position.

FIG. 2A illustrates an isometric view of a portion of forceps 200 in a closed position. FIG. 2B illustrates an isometric view of a portion of the forceps 200 in a partially open position. FIG. 2C illustrates an isometric view of a portion of the forceps 200 in an open position. FIGS. 2A-2C are discussed below concurrently.

The forceps 200 can include an end effector 202 that can be connected to a handle (such as the handle 104). The end effector 202 can include jaws 206a and 206b, an outer shaft 208, grip plates 209a and 209b, an inner shaft 210, a blade assembly 212, a pivot pin 214, a drive pin 216, and a guide pin 218. The jaw 206a can include flanges 220a and 220b, and the jaw 206b can include flanges 222a and 222b. The grip plate 209a can include a blade slot 224a and the grip plate 209b can include a blade slot 224b. The blade assembly 212 can include a blade 212a and a shaft 212b. FIGS. 2A-2C also show orientation indicators Proximal and Distal and a longitudinal axis A1.

The components of the forceps 200 can each be comprised of materials such as one or more of metals, plastics, foams, elastomers, ceramics, composites, combinations thereof, or the like. Materials of some components of the forceps 200 are discussed below in further detail.

The jaws 206a and 206b can be rigid or semi-rigid members configured to engage tissue. The jaws 206a and 206b can be coupled to the outer shaft 208, such as pivotably coupled, via the pivot pin 214. The pivot pin 214 can extend through a portion of the jaws 206a and 206b (such as a bore of each of the jaws 206a and 206b) such that the pivot pin 214 can be received by outer arms of the outer shaft 208. In other examples, the jaws 206a and 206b can be pivotably coupled to the outer shaft 208 via a boss or bosses of the outer shaft 208. In another example, the jaws 206a and 206b can include a boss (or bosses) receivable in bores of the outer shaft 208 to pivotably couple the jaws 206a and 206b to the outer shaft 208. In another example, outer shaft 208 can include a boss (or bosses) receivable in bores of the jaws 206a and 206b to pivotably couple the jaws 206a and 206b to the outer shaft 208.

The flanges 220a and 220b (which can be a set of flanges, that is, two flanges) can be rigid or semi-rigid members located at a proximal portion of the jaw 206a. Similarly, the flanges 222a and 222b can be rigid or semi-rigid members located at a proximal portion of the jaw 206b. In some examples, the flanges 220 can be positioned laterally outward of the inner flanges 222. In other examples, the flanges 220 and 222 can be interlaced.

The grip plates 209a and 209b of the jaws 206a and 206b can each be a rigid or semi-rigid member configured to engage tissue and/or the opposing jaw to grasp tissue, such as during an electrosurgical procedure. One or more of the grip plates 209a and 209b can include one or more of serrations, projections, ridges, or the like configured to increase engagement pressure and friction between the grip plates 209a and 209b and tissue. The flanges 220 of the upper jaw 206a can extend proximally away from the grip plate 209a and 209b, and in some examples, substantially downward when the upper jaw 206a is in the open and partially open positions (as shown in FIGS. 2B and 2C, respectively). Similarly, the flanges 222 of the lower jaw 206b can extend proximally away from the grip plate, and in some examples, substantially upward when the upper jaw 206a is in the open and partially open positions (as shown in FIGS. 2B and 2C, respectively), such that the jaws 206a and 206b and flanges 220 and 222 operate to open and close in a scissoring manner. The jaws 206a and 206b can each include an electrode configured to deliver electricity to tissue (optionally through the grip plates 209a and 209b), and a frame supporting the electrode. The blade slots 224a and 224b of the grip plates 209a and 209b can together be configured to receive a blade between the jaws 206a and 206b, when the jaws are moved out of the open position. In some examples, only one blade slot may be used.

Each of the inner shaft 210 and the outer shaft 208 can be a rigid or semi-rigid and elongate body having a geometric shape of a cylinder, where the shape of the inner shaft 210 matches the shape of the outer shaft 208. In some examples, the inner shaft 210 and the outer shaft 208 can have other shapes such as an oval prism, a rectangular prism, a hexagonal prism, an octagonal prism, or the like. In some examples, the shape of the inner shaft 210 can be different from the shape of the outer shaft 208.

The inner shaft 210 can extend substantially proximally to distally along the axis A1, which can be a longitudinal axis. In some examples, the axis A1 can be a central axis. Similarly, the outer shaft 208 can extend substantially proximally to distally along the axis A1. In some examples, the axis A1 can be a central axis of one or more of the inner shaft 210 and the outer shaft 208. The inner shaft 210 can include an axial bore extending along the axis A1. The outer shaft 208 can also include an axial bore extending along the axis A1. The inner shaft 210 can have an outer dimension (such as an outer diameter) smaller than an inner diameter of the outer shaft 208 such that the inner shaft 210 can be positioned within the outer shaft 208 and such that the inner shaft 210 can be translatable in the outer shaft 208 along the axis A1. The inner shaft 210 can also be referred to as a drive shaft 210, a cam shaft 210, or an inner tube 210. The outer shaft 208 can also be referred to as an outer tube 208.

The blade 212a can be an elongate cutting member at a distal portion of the blade assembly 212. The blade 212a can include one or more sharpened edges configured to cut or resect tissue or other items. The blade assembly 212 can be located within the outer shaft 208 (and can be located within the inner shaft 210). The blade 212a can extend along (and optionally parallel with) the axis A1. The blade 212a can be translatable with respect to the inner shaft 210 and the outer shaft 208 to extend between (or into) the first jaw 206a and the second jaw 206b, such as along the blade slots 224a and 224b. In some examples, the blade 212a can extend axially through the inner shaft 210 offset from the axis A1. In some examples, the blade 212a the blade can extend axially through the flanges 220 and 222 to extend into the jaws 206, such that the blade 212a is in a position laterally inward of the first set of flanges 220 and the second set of flanges 222. In other examples, the blade 212a can be positioned laterally inward of some flanges (220 or 222) and laterally outward of other flanges (220 or 222). In some examples, each jaw 206 can include only a single flange 220 and 222. In such an example, the blade 212a can extend between (laterally inward of) the two flanges 220 and 222 or can extend laterally outward of the flanges 220 and 222.

The blade 212a can also be a translating member or electrosurgical component other than a blade. For example, the translating member 212a can be an advancing electrosurgical electrode configured to cut tissue, such as a blunt electrode, an electrosurgical blade, a needle electrode, or a snare electrode.

The guide 218, the drive pin 216, and the pivot pin 214 can each be a rigid or semi-rigid pin, such as a cylindrical pin. The guide 218, the drive pin 216, and the pivot pin 214 can have other shapes in other examples, such as rectangular, square, oval, or the like. In some examples, the pivot pin 214 can have a size (such as a diameter) that is larger than the drive pin 216, as discussed below in further detail. Each pin can have a smooth surface to help reduce surface friction between the pins and components of the forceps 200, such as between the pivot pin 214 and the outer shaft 208 or the drive pin 216 and the flanges 220 and 222. Each of the guide 218, the drive pin 216, and the pivot pin 214 can be other components such as one or more projections, bosses, arms, or the like.

The guide 218 can be not omitted in some examples, such that the drive pin 216 and the pivot pin 214 can connect the inner shaft 210 to the outer shaft 208 (such as through the jaws 206).

In operation, the inner shaft 210 can be translated using an actuator (such as the lever 116 of FIG. 1). The inner shaft 210 can translate with respect to the outer shaft 208 to move the drive pin 216. The drive pin 216 can engage the flanges 220 and 222 to move the flanges 220 and 222 between open and closed positions, which can cause the jaws 206a and 206b to move between open and closed positions. Further details and operation of the forceps 200 are discussed below with respect to FIGS. 3A and 3B.

Figure 3A:
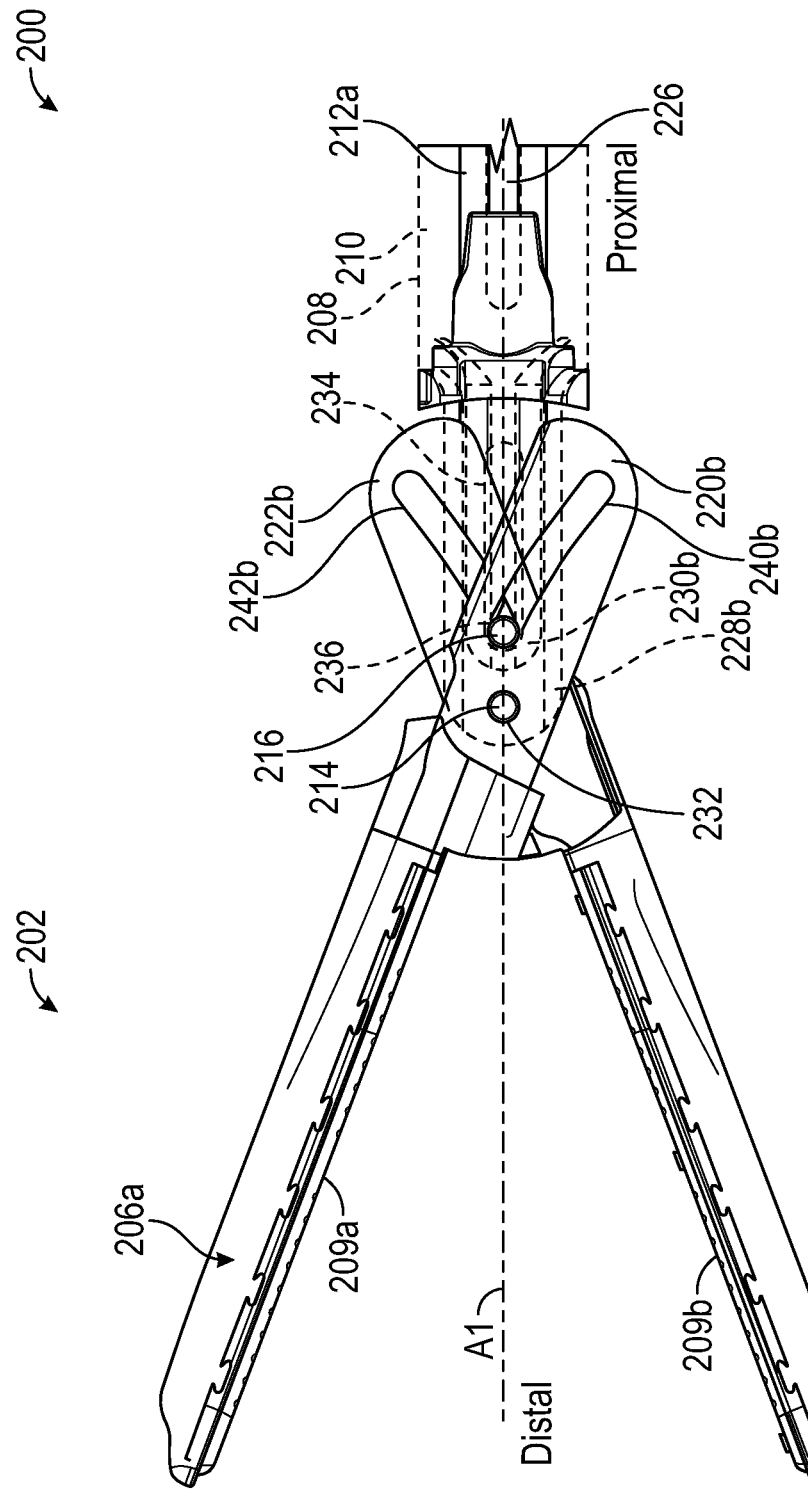
FIG. 3A illustrates a side view of a portion of forceps in an open position.
Figure 3B:
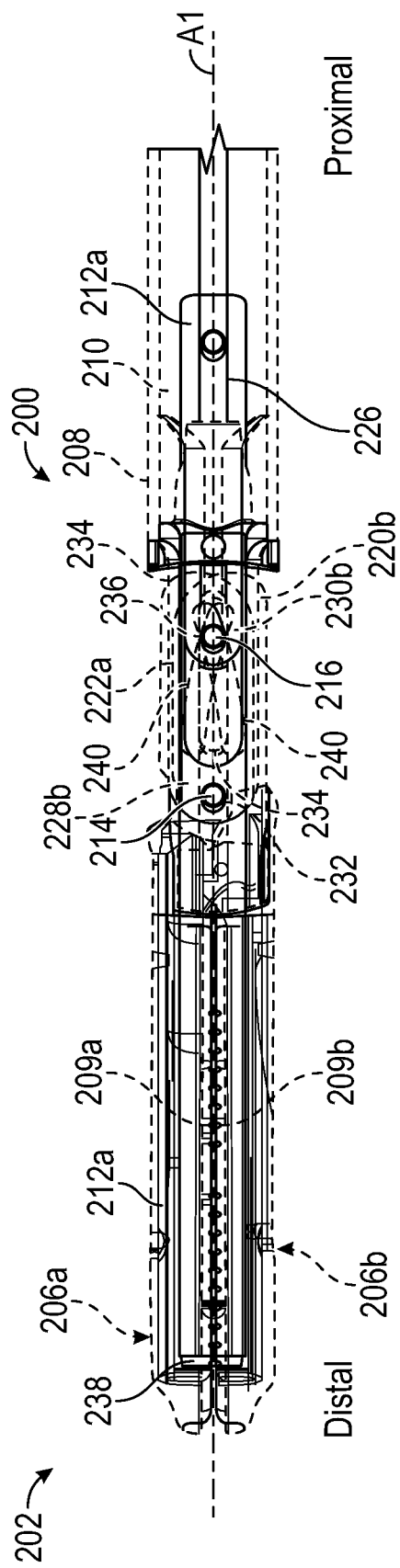
FIG. 3B illustrates an isometric view of a portion of forceps in a closed position with a blade extended.
Figure 3C:
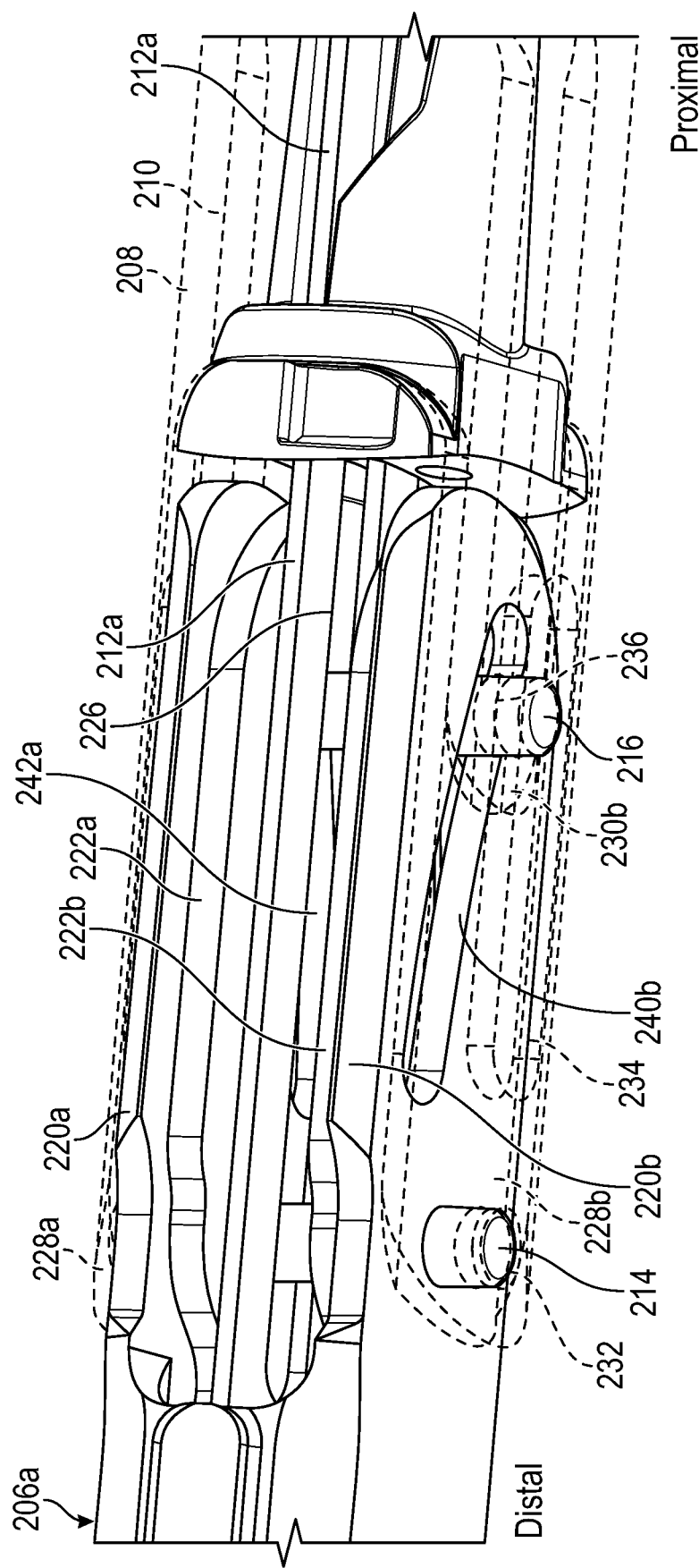
FIG. 3C illustrates an isometric view of a portion of forceps.

FIG. 3A illustrates a side view of a portion of the forceps 200 in an open position with the blade retracted and with the inner shaft 210 and the outer shaft 208 in phantom. FIG. 3B illustrates an isometric view of a portion of the forceps 200 in a closed position with the blade extended and with the inner shaft 210, the outer shaft 208, and the jaws 206a and 206b in phantom. FIG. 3C illustrates an isometric view of the forceps 200 in a closed position. FIGS. 3A-3C are discussed below concurrently. FIGS. 3A-3C show orientation indicators Proximal and Distal and the axis A1.

The forceps 200 of FIGS. 3A-3C can be consistent with FIGS. 1A-2C discussed above; FIGS. 3A-3C show additional details of the forceps 200. For example, FIG. 3A shows that the outer shaft 208 can include outer arms 228a and 228b and the inner shaft 210 can include inner arms 230a and 230b.

The outer arms 228a and 228b can extend distally from a distal portion of the outer shaft 208 to form a fork or clevis. In some examples, the outer arms 228a and 228b can extend distally beyond the inner arms 230a and 230b to receive the pivot pin 214 therein to secure the flanges 220 and 222 (and therefore the jaws 206a and 206b) to the outer shaft 208. The inner arms 230a and 230b (distal arms) of the inner shaft 210 can extend distally from a distal portion of the inner shaft 210 and can be positioned laterally outward of the flanges 220 and 222. In some examples, the inner arms 230a and 230b can together form a fork or clevis.

The outer arms 228a and 228b can include a pivot pin guide 232, which can be a bore, guide, slot, track, or the like, configured to receive and retain at least a portion of the pivot pin 214. The pivot pin guide 232 can be substantially perpendicular to the axis A1 and the pivot pin guide 232 can be centered on the axis A1 near the distal end of the outer shaft 208. Also, the pivot pin 214 can be substantially perpendicular to the axis A1 and the pivot pin 214 can be centered on the axis A1 near the distal end of the outer shaft 208.

The outer arms 228a and 228b can also include an outer track 234, which can be guides, slots, tracks, or the like configured to receive and retain at least a portion of the drive pin 216. The outer track 234 (of each of the outer arms 228a and 228b) can be configured (e.g., sized and shaped) to allow the drive pin 216 to translate therein. In some examples, axial movement, vertical movement, or rotation of the guide pin 218 with respect to the outer shaft 208 can be limited by contact between the guide pin 218 and the outer track(s) 234. The inner arms 230a and 230b can include a drive pin bore 236, which can be a bore, guide, slot, track, or the like, configured to receive and retain at least a portion of the drive pin 216.

FIGS. 3A-3C also show that the blade 212a can include a blade track 226, which can be a slot, track, guide, or the like extending into or through the blade 212a. The blade track 226 can receive the pivot pin 214 and drive pin 216 therein or therethrough to allow translation of the blade 212a while helping to limit non-translational movement of the blade 212a with respect to the inner shaft 210 and the outer shaft 208. FIG. 3B also shows that the blade 212a can include a sharpened end 238, which can be a distal sharpened edge or portion of the blade 212a. In other examples, other portions of the blade 212a can be sharpened, such as a top or bottom edge of the blade 212a. FIGS. 3A-3C also show that the blade 212a can be positioned laterally inward of the inner arms 230a and 230b and can be positioned laterally inward of the outer arms 228a and 228b.

FIGS. 3A-3C further show that the flanges 220a and 220b can include tracks 240a and 240b and the flanges 222a and 222b can include tracks 242a and 242b. The tracks 240 of the flanges 220 and the tracks 242 of the flanges 222 can each be a track, channel, path, or slot in the flanges 220 and 222, respectively. In some examples, the tracks 240 and 242 can be located proximally of the pivot pin 214 when the pivot pin 214 is coupled to the jaws 206a and 206b (and optionally to the outer shaft 208). The tracks 240 and 242 can be shaped to receive the drive pin 216 therein. In some examples, the tracks 240 and 242 can be slots or channels configured to receive the drive pin 216 therethrough to connect the drive shaft 210 (such as the inner arm 230a or the inner arm 230b) to the flanges 220 and 222 (and therefore to the jaws 206a and 206b). The tracks 240 and 242 can be configured to allow the drive pin 216 to travel along the tracks 240 and 242 simultaneously to open and close the jaws.

In some examples where the guide 218 is included, the blade track 226 can be extended proximally to encompass the guide pin 218, which can be sized similarly to the drive pin 216.

In operation of some examples, a handle (such as those discussed above) can be operated to translate the inner shaft 210 within (and with respect to) the outer shaft 208. For example, distal translation of the inner shaft 210 with respect to the outer shaft 208 can cause the drive pin 216 to translate distally causing the jaws 206a and 206b to move from a closed position (as shown in FIGS. 2A and 3A) to an intermediate position (as shown in FIG. 2B) to an open position (as shown in FIGS. 2C and 3B). Conversely, proximal translation of the inner shaft 210 can cause the drive pin 216 to translate proximally to move the jaws 206a and 206b to the closed position, such that the drive pin 216 can translate to cause the jaws 206a and 206b to open and close in a scissoring manner. In other examples, the action can be reversed such that distal movement of the inner shaft 210 can cause the jaws 206a and 206b to move toward a closed position and proximal movement of the inner shaft 210 can cause the jaws 206a and 206b toward an open position.

More specifically, distal translation of the inner shaft 210 can cause the drive pin 216 to translate distally within the outer slots 234 of the outer arms 228, such as to help guide axial translation of the drive pin 216 by helping to limit non-axial movement of the inner shaft 210 with respect to the outer shaft 208. As the drive pin 216 translates distally in the outer slots 234, the drive pin 216 can translate distally along (such as within) the tracks 240 of the flanges 220 of the upper jaw 206a and along the tracks 242 of the flanges 222 of the lower jaw 206b. Because the tracks 240 and 242 can be angled and/or curved along the flanges 220 and 222, respectively, and because the tracks 240 and 242 can be oppositely oriented with respect to each other, distal translation of the drive pin 216 can cause the jaws 206a and 206b to open in a scissor type movement.

To close the jaws, the inner shaft 210 can be translated proximally to proximally translate the drive pin 216, which can cause the drive pin 216 to translate proximally within the outer slots 234. As the drive pin 216 translates proximally in the outer slots 234, the drive pin 216 can translate proximally along (such as within) the tracks 240 of the flanges 220 of the upper jaw 206a and along the tracks 242 of the flanges 222 of the lower jaw 206b. Proximal translation of the drive pin 216 can cause the jaws 206a and 206b to close in a scissor type movement.

When the jaws 206a and 206b are in the partially closed position (as shown in FIG. 2B) or when the jaws are not in a fully open position, the blade 212a can be partially extended into the jaws 206a and 206b such as to cut tissue between the jaws 206a and 206b. The blade 212a can be extended by operating the trigger 120 of the handle (or other actuator), as discussed above. When the jaws 206a and 206b are in the closed position (as shown in FIG. 2A), the blade 212a can be fully extended into the jaws 206a and 206b along the blade guides 224a and 224b such that the sharpened edge 238 of the blade 212a can cut tissue between the jaws 206a and 206b. Using these operations, a physician can use the forceps 200 to grasp tissue using the jaws 206a and 206b, resect tissue using the blade 212a, and remove tissue of a patient.

When the blade 212a translates (or reciprocates) between an extended and retracted position, the blade 212a can be guided by engagement between the blade track 226 and the pivot pin 214 and the drive pin 216. This interaction is discussed in further detail below with respect to FIGS. 4A and 4B.

Figure 4A:
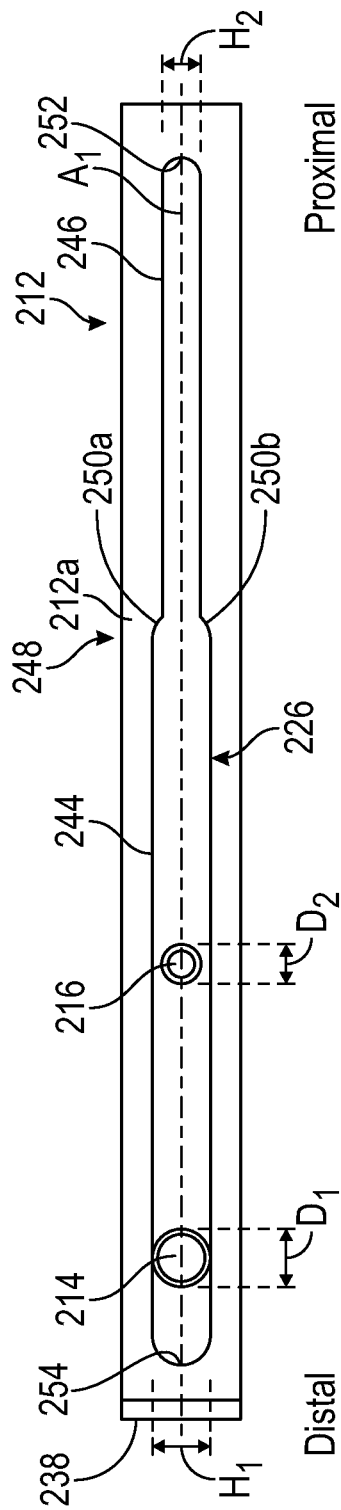
FIG. 4A illustrates an isometric view of a portion of forceps with a blade in a retracted position.
Figure 4B:
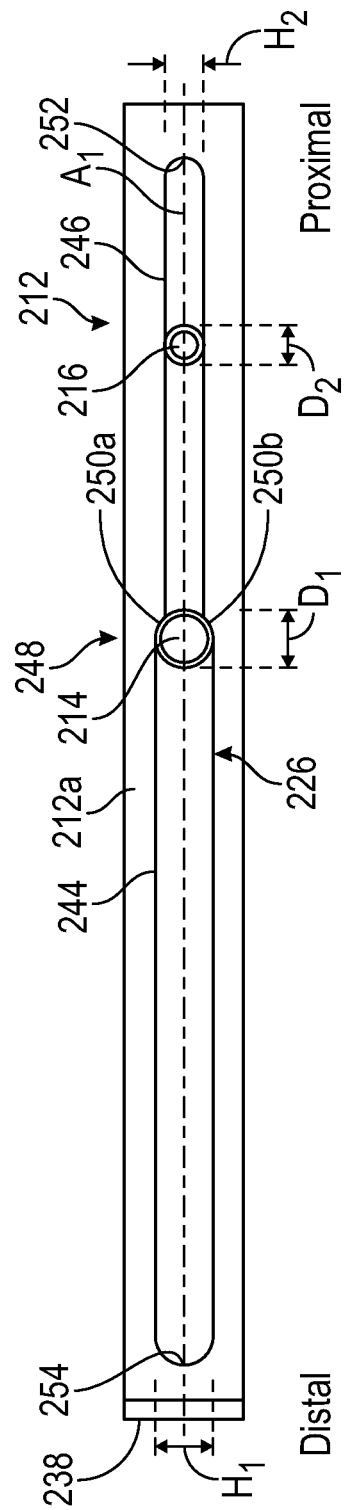
FIG. 4B illustrates an isometric view of a portion of forceps with a blade in an extended position.

FIG. 4A illustrates an isometric view of the blade assembly 212 in a retracted position. FIG. 4B illustrates an isometric view of the blade assembly 212 in an extended position. FIGS. 4A and 4B are discussed below concurrently.

The blade assembly 212 includes the blade 212a, which can include the blade track 226 and the edge 238. The blade track 226 can include a distal portion 244 (which can include a height H1), a proximal portion 246 (which can include a height H2), and a transition 248 (which can include curved portions 250a and 250b). Also shown in FIGS. 4A and 4B are the pivot pin 214 (which can have a diameter of D1) and the drive pin 216 (which can have a diameter of D2). FIGS. 4A and 4B also show the axis A1 and orientation indicators Proximal and Distal.

The pivot pin 214 can extend into the blade track 226 to limit distal translation of the blade 212a along the longitudinal axis A1 with respect to the jaws 206a and 206b. The drive pin 216 can also extend into the blade track 226 but can be sized not to interact with the distal portion 244 of the blade track 226. The pivot pin 214 can be especially effective at limiting distal translation of the blade 212a with respect to the jaws 206 because it is beneficial for an end of distal travel of the blade 212a to be positioned accurately relative to an axial position or extent of the jaw or jaws 206, because the pivot pin 214 controls the axial position of the jaws 206 with respect to the outer shaft 208, whereas the drive pin 216 moves with respect to the outer shaft 208 and therefore the jaws 206.

More specifically, the pivot pin 214 can define the pivot pin diameter D1 and the drive pin 216 can define the drive pin diameter D2. In some examples, the pivot pin diameter D1 can be larger than the drive pin diameter D2, where the pivot pin 214 can be located or positioned distal to the drive pin 216. Also, the distal track portion 244 can define the distal height H1 and the proximal track portion 246 can define the proximal height H2 where the distal height H1 can be larger than the proximal height H2.

The distal height H1 can be configured to receive the pivot pin 214 and the drive pin 216 where the pivot pin 214 is located proximal of the drive pin 216. The drive pin 216 can extend in or through the distal portion 244. The proximal height H2 of the proximal portion 246 can be sized to receive the drive pin 216 therein (or therethrough) and can be sized smaller than the pivot pin diameter D1 such that the pivot pin 214 cannot enter the proximal portion 246. That is, the proximal portion 246 can be configured to engage the pivot pin 214 to limit distal translation of the blade 212a with respect to the inner shaft 210, the outer shaft 208, or the jaws 206.

The proximal height H2 can be larger than the diameter D2 but can smaller than the diameter D1. In some examples, the proximal height H2 can be minimally larger than the diameter D2 such as to help limit non-axial movement of the blade 212a along the drive pin 216. Similarly, the distal height H2 can be larger than the diameter D1 and the diameter D2 and the distal height H1 can be minimally larger than the diameter D1 such as to help limit non-axial movement of the blade 212a along the pivot pin 214.

In some examples, the blade 212a can form the transition 248 between the distal track portion 244 and the proximal track portion 246, where the transition 248 can be configured to engage the pivot pin 214 to limit distal translation of the blade 212a with respect to the shaft (e.g., the outer shaft 208 or the inner shaft 210). The transition 248, which can include the curved portions 250a and 250b, can be shaped complementary to the pivot pin 214. For example, a curvature of the curved portions 250a and 250b can match a curvature of the pivot pin 214, which can help limit wear on the pivot pin 214 and the transition 248 caused by contact between the pivot pin 214 and the transition 248. The curved portions 250 can also help to guide the drive pin 216 into the proximal portion 246 during translation of the blade 212a.

In operation of some examples, as the blade 212a is moved from a retracted position (FIG. 4A) to an extended position (FIG. 4B), the blade 212a can move distally with respect to the drive pin 216 and the pivot pin 214. Such translation of the blade 212a can cause the drive pin to move from the distal portion 244 of the blade track 226 into the proximal portion 246 of the blade track. Such translation of the blade 212a can also cause the pivot pin 214 to move along and within the distal portion 244 of the blade track 226 until the pivot pin 214 contacts the blade 212a at a proximal termination of the distal portion 244 of the blade track 226. The proximal termination can be the transition 248, which can help prevent the pivot pin 214 from entering the proximal portion 246, helping to and precisely control distal translation of the blade 212a with respect to the jaws 206, the inner shaft 210, or the outer shaft 208.

Also, as shown in FIGS. 4A and 4B, the blade track 226 can include a proximal termination 252 and a distal termination 254. The proximal termination 252 can be a termination of the track 226 at a proximal portion of the blade 212a and the distal termination can be a termination of the track 226 at a distal portion of the blade 212a. In some examples, the proximal termination 252 can be curved, such as to have a shape complimentary to the drive pin 216 to help limit wear on the blade 212a and the drive pin 216. In some examples, the proximal termination 252 can be curved, such as to have a shape complimentary to the guide pin 218 to help limit wear on the blade 212a and the guide pin 218. In some examples, the distal termination 254 can be curved, such as to have a shape complimentary to the pivot pin 214 to help limit wear on the blade 212a and the pivot pin 214 when the pivot pin 214 engages the distal termination 254 to help limit proximal translation of the blade 212a with respect to the outer shaft 208.

NOTES AND EXAMPLES

The following, non-limiting examples, detail certain aspects of the present subject matter to solve the challenges and provide the benefits discussed herein, among others.

Example 1 is a surgical forceps comprising: a shaft defining a longitudinal axis; a pivot pin located at a distal portion of the shaft; a first jaw connected to the shaft; a second jaw pivotably coupled to the shaft by the pivot pin; and a blade located laterally inward of the shaft, the blade including a blade track, and the pivot pin extending into the blade track to limit distal translation of the blade along the longitudinal axis with respect to the first jaw and the second jaw.

In Example 2, the subject matter of Example 1 optionally includes a drive pin; and a drive shaft extending along the longitudinal axis and connected to the second jaw by the drive pin, the drive shaft translatable with respect to the shaft to move the drive pin to move the second jaw between an open position and a closed position.

In Example 3, the subject matter of Example 2 optionally includes wherein the drive pin extends into the blade track.

In Example 4, the subject matter of Example 3 optionally includes wherein the drive pin defines a drive pin diameter and the pivot pin defines a pivot pin diameter that is larger than the drive pin diameter.

In Example 5, the subject matter of Example 4 optionally includes wherein the blade track includes: a distal track portion defining a distal size configured to receive the pivot pin and the drive pin therein; and a proximal track portion defining a proximal size configured to receive the drive pin therein.

In Example 6, the subject matter of Example 5 optionally includes wherein proximal track portion is configured to engage the pivot pin to limit distal translation of the blade with respect to the shaft.

In Example 7, the subject matter of any one or more of Examples 5-6 optionally include wherein the blade forms a transition between the distal track portion and the proximal track portion that is configured to engage the pivot pin to limit distal translation of the blade with respect to the shaft.

In Example 8, the subject matter of any one or more of Examples 1-7 optionally include wherein the transition is shaped complementary to the pivot pin.

In Example 9, the subject matter of any one or more of Examples 5-8 optionally include wherein the proximal portion is engageable with the pivot pin to limit proximal translation of the blade with respect to the shaft.

In Example 10, the subject matter of any one or more of Examples 2-9 optionally include wherein the drive pin defines a drive pin diameter and wherein a height of the blade track is larger than the drive pin diameter.

In Example 11, the subject matter of any one or more of Examples 1-10 optionally include wherein the longitudinal axis defines a central axis of the shaft.

Example 12 is a surgical forceps comprising: a shaft defining a longitudinal axis; a pivot pin located at a distal portion of the shaft; an end effector connected to the shaft by the pivot pin; and a translating member positioned laterally inward of the shaft, the translating member including a track, and the pivot pin extending into the track to limit distal translation of the translating member along the longitudinal axis with respect to the end effector.

In Example 13, the subject matter of Example 12 optionally includes wherein the track includes a distal portion engageable with the pivot pin to limit proximal translation of the translating member with respect to the shaft.

In Example 14, the subject matter of any one or more of Examples 12-13 optionally include a drive pin; and a drive shaft extending along the longitudinal axis and connected to the end effector by the drive pin, the drive shaft translatable with respect to the shaft to move the drive pin to operate the end effector.

In Example 15, the subject matter of Example 14 optionally includes wherein the drive pin extends into the track.

In Example 16, the subject matter of Example 15 optionally includes wherein the drive pin defines a drive pin diameter and the pivot pin defines a pivot pin diameter that is larger than the drive pin diameter.

In Example 17, the subject matter of Example 16 optionally includes wherein the track includes: a distal track portion defining a distal size configured to receive the pivot pin and the drive pin therein; and a proximal track portion defining a proximal size configured to receive the drive pin therein.

In Example 18, the subject matter of Example 17 optionally includes wherein proximal track portion is configured to engage the pivot pin to limit distal translation of the translating member with respect to the shaft.

In Example 19, the subject matter of any one or more of Examples 17-18 optionally include wherein the translating member forms a transition between the distal track portion and the proximal track portion that is configured to engage the pivot pin to limit distal translation of the translating member with respect to the shaft.

In Example 20, the subject matter of any one or more of Examples 12-19 optionally include wherein the transition is shaped complementary to the pivot pin.

In Example 21, the subject matter of any one or more of Examples 17-20 optionally include wherein the track includes a distal portion engageable with the pivot pin to limit proximal translation of the translating member with respect to the shaft.

Example 22 is a surgical forceps comprising: a shaft defining a longitudinal axis; a pivot pin located at a distal portion of the shaft; a drive pin located at the distal portion of the shaft at a location proximal of the pivot pin; a first jaw connected to the shaft; a second jaw pivotably coupled to the shaft by the pivot pin with respect to the first jaw; and a blade located laterally inward of the shaft, the blade including a blade track, the pivot pin and the drive pin extending into the blade track.

In Example 23, the subject matter of Example 22 optionally includes wherein the blade track includes: a distal track portion defining a distal size configured to receive the pivot pin and the drive pin therein; and a proximal track portion defining a proximal size configured to receive the drive pin therein.

In Example 24, the subject matter of Example 23 optionally includes wherein proximal track portion is configured to engage the pivot pin to limit distal translation of the blade with respect to the shaft.

In Example 25, the subject matter of any one or more of Examples 23-24 optionally include wherein the blade forms a transition between the distal track portion and the proximal track portion that is configured to engage the pivot pin to limit distal translation of the blade with respect to the shaft.

In Example 26, the subject matter of any one or more of Examples 22-25 optionally include wherein the transition is shaped complementary to the pivot pin.

In Example 27, the apparatuses or method of any one or any combination of Examples 1-26 can optionally be configured such that all elements or options recited are available to use or select from.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A surgical forceps comprising: a shaft defining a longitudinal axis; a pivot pin located at a distal portion of the shaft; a first jaw connected to the shaft; a second jaw pivotably coupled to the shaft by the pivot pin; and a blade located laterally inward of the shaft, the blade including a blade track, and the pivot pin extending into the blade track and engageable with the blade track to limit distal translation of the blade along the longitudinal axis with respect to the first jaw and the second jaw, a drive pin located at a distal portion of the shaft at a location proximal of the pivot pin, and wherein the drive pin extends into the blade track.

2. The surgical forceps of claim 1, further comprising: a drive shaft extending along the longitudinal axis and connected to the second jaw by the drive pin, the drive shaft translatable with respect to the shaft to move the drive pin to move the second jaw between an open position and a closed position.

3. The surgical forceps of claim 2, wherein the drive pin defines a drive pin diameter and the pivot pin defines a pivot pin diameter that is larger than the drive pin diameter.

4. The surgical forceps of claim 3, wherein the blade track includes:
 a distal track portion defining a distal size configured to receive the pivot pin and the drive pin therein; and
 a proximal track portion defining a proximal size configured to receive the drive pin therein.

5. The surgical forceps of claim 4, wherein the proximal track portion is configured to engage the pivot pin to limit distal translation of the blade with respect to the shaft.

6. The surgical forceps of claim 4, wherein the blade forms a transition between the distal track portion and the proximal track portion that is configured to engage the pivot pin to limit distal translation of the blade with respect to the shaft.

7. The surgical forceps of claim 6, wherein the transition is shaped complementary to the pivot pin.

8. The surgical forceps of claim 4, wherein the proximal track portion is engageable with the pivot pin to limit proximal translation of the blade with respect to the shaft.

9. The surgical forceps of claim 2, wherein the drive pin defines a drive pin diameter and wherein a height of the blade track is larger than the drive pin diameter.

10. The surgical forceps of claim 1, wherein the longitudinal axis defines a central axis of the shaft.

11. A surgical forceps comprising: a shaft defining a longitudinal axis; a pivot pin located at a distal portion of the shaft; an end effector connected to the shaft by the pivot pin; and a translating member positioned laterally inward of the shaft, the translating member including a track, and the pivot pin engageable with the track to limit distal translation of the translating member along the longitudinal axis with respect to the end effector, a drive pin located at a distal portion of the shaft at a location proximal of the pivot pin, and wherein the drive pin extends into the track.

12. The surgical forceps of claim 11, wherein the track includes a distal portion engageable with the pivot pin to limit proximal translation of the translating member with respect to the shaft.

13. The surgical forceps of claim 11, further comprising: a drive shaft extending along the longitudinal axis and connected to the end effector by the drive pin, the drive shaft translatable with respect to the shaft to move the drive pin to operate the end effector.

14. The surgical forceps of claim 13, wherein the drive pin defines a drive pin diameter and the pivot pin defines a pivot pin diameter that is larger than the drive pin diameter.

15. The surgical forceps of claim 14, wherein the track includes:
 a distal track portion defining a distal size configured to receive the pivot pin and the drive pin therein; and
 a proximal track portion defining a proximal size configured to receive the drive pin therein.

16. The surgical forceps of claim 15, wherein the proximal track portion is configured to engage the pivot pin to limit distal translation of the translating member with respect to the shaft.

17. The surgical forceps of claim 15, wherein the translating member forms a transition between the distal track portion and the proximal track portion that is configured to engage the pivot pin to limit distal translation of the translating member with respect to the shaft.

18. The surgical forceps of claim 17, wherein the transition is shaped complementary to the pivot pin.

19. A surgical forceps comprising:
 a shaft defining a longitudinal axis;
 a pivot pin located at a distal portion of the shaft;
 a drive pin located at the distal portion of the shaft at a location proximal of the pivot pin;
 a first jaw connected to the shaft;
 a second jaw pivotably coupled to the shaft by the pivot pin with respect to the first jaw; and
 a blade located laterally inward of the shaft, the blade including a blade track, the pivot pin and the drive pin extending into the blade track, the blade track engageable with the pivot pin to limit distal translation of the blade along the longitudinal axis.

20. The surgical forceps of claim 19, wherein the blade track includes:
 a distal track portion defining a distal size configured to receive the pivot pin and the drive pin therein; and
 a proximal track portion defining a proximal size configured to receive the drive pin therein.

* * * * *